United States Patent
Kurtz et al.

(10) Patent No.: US 11,806,554 B2
(45) Date of Patent: Nov. 7, 2023

(54) MULTI-CHANNEL REAL-TIME PHASE MODULATION FOR EMI REDUCTION IN AN ULTRASOUND DEVICE

(71) Applicant: Profound Medical Inc., Mississauga (CA)

(72) Inventors: Ron Kurtz, Oakville (CA); Patrick Leonard, Toronto (CA); Xiaoyu Zhang, Mississauga (CA)

(73) Assignee: Profound Medical Inc., Mississauga (CA)

( * ) Notice: Subject to any disclaimer, the term of this patent is extended or adjusted under 35 U.S.C. 154(b) by 1621 days.

(21) Appl. No.: 15/723,850

(22) Filed: Oct. 3, 2017

(65) Prior Publication Data
US 2019/0099624 A1 Apr. 4, 2019

(51) Int. Cl.
*A61N 7/02* (2006.01)
*A61N 7/00* (2006.01)
*A61B 90/00* (2016.01)

(52) U.S. Cl.
CPC .......... *A61N 7/02* (2013.01); *A61B 2090/374* (2016.02); *A61N 2007/0078* (2013.01); *A61N 2007/0095* (2013.01); *A61N 2007/025* (2013.01)

(58) Field of Classification Search
CPC ................ A61N 7/02; A61N 2007/025; A61N 2007/0095; A61N 2007/0078; A61B 2090/374
See application file for complete search history.

(56) References Cited

U.S. PATENT DOCUMENTS

| | | | | |
|---|---|---|---|---|
| 6,221,018 B1* | 4/2001 | Ramamurthy | ......... | A61B 8/481 600/443 |
| 6,506,154 B1* | 1/2003 | Ezion | .................... | G10K 11/341 600/437 |
| 6,599,248 B1* | 7/2003 | Tamura | ............... | G01S 15/8979 600/454 |
| 6,666,833 B1* | 12/2003 | Friedman | ................. | A61N 7/02 600/407 |

(Continued)

FOREIGN PATENT DOCUMENTS

| | | |
|---|---|---|
| CN | 1596432 A | 3/2005 |
| CN | 1814320 A | 8/2006 |

(Continued)

OTHER PUBLICATIONS

Satir et al., "Phase and Amplitude Modulation Methods for Nonlinear Ultrasound Imaging with CMUTs", Aug. 2016, IEEE Trans Ultrasonic Ferroelectrics Frequency Control (Year: 2016).*

(Continued)

*Primary Examiner* — Patricia J Park
*Assistant Examiner* — Adil Partap S Virk
(74) *Attorney, Agent, or Firm* — Intrinsic Law Corp.

(57) ABSTRACT

Methods for reducing electromagnetic interference arising from use of multiple ultrasound transducers in an array, particularly inside a human body that is inside a magnetic resonance imaging device. Electrical signals driving the transducers are offset in phase with respect to one another so as to achieve maximum offset of electrical and magnetic fields arising from such signals and transducers. Phase offsets are dynamically adjusted to respond to changes in driving amplitudes and frequencies so as to maintain optimal reduction of electromagnetic interference.

3 Claims, 11 Drawing Sheets

(56) References Cited

U.S. PATENT DOCUMENTS

| | | | |
|---|---|---|---|
| 2003/0028111 A1 | 2/2003 | Vaezy et al. | |
| 2004/0087857 A1* | 5/2004 | Napolitano | G01S 7/52046 |
| | | | 600/443 |
| 2010/0125292 A1* | 5/2010 | Wiener | A61B 17/320068 |
| | | | 606/169 |
| 2013/0158385 A1* | 6/2013 | Barnes | A61N 7/00 |
| | | | 600/411 |
| 2016/0296975 A1 | 10/2016 | Lukacs et al. | |
| 2016/0331350 A1* | 11/2016 | Duncan | A61B 8/481 |
| 2018/0064364 A1* | 3/2018 | Oziel | A61B 5/0042 |
| 2018/0146976 A1* | 5/2018 | Clauda | A61B 17/2909 |
| 2018/0353239 A1* | 12/2018 | Stone | A61B 18/1206 |
| 2021/0275834 A1* | 9/2021 | Duchon | A61K 35/19 |

FOREIGN PATENT DOCUMENTS

| | | | |
|---|---|---|---|
| CN | 101947129 A | 1/2011 | |
| CN | 102711914 A | 10/2012 | |
| CN | 103212165 A | 7/2013 | |
| CN | 105073016 A | 11/2015 | |
| CN | 105162356 A | 12/2015 | |

OTHER PUBLICATIONS

ISA, "International Search Report", PCT/IB2017/001388, dated Jun. 7, 2018.
CIPO, "Requisition by the Examiner", CA Application No. 3,075,451, dated Apr. 22, 2021.
CNIPA, "Office Action", CN Application No. 201780095470.2, dated Apr. 27, 2021.

* cited by examiner

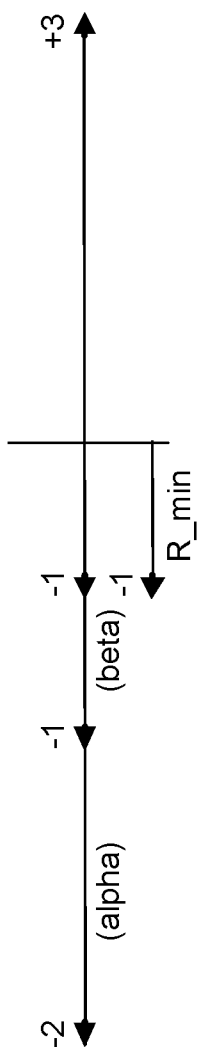
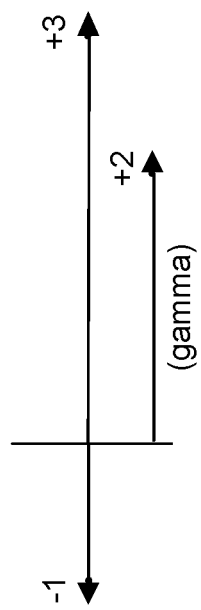

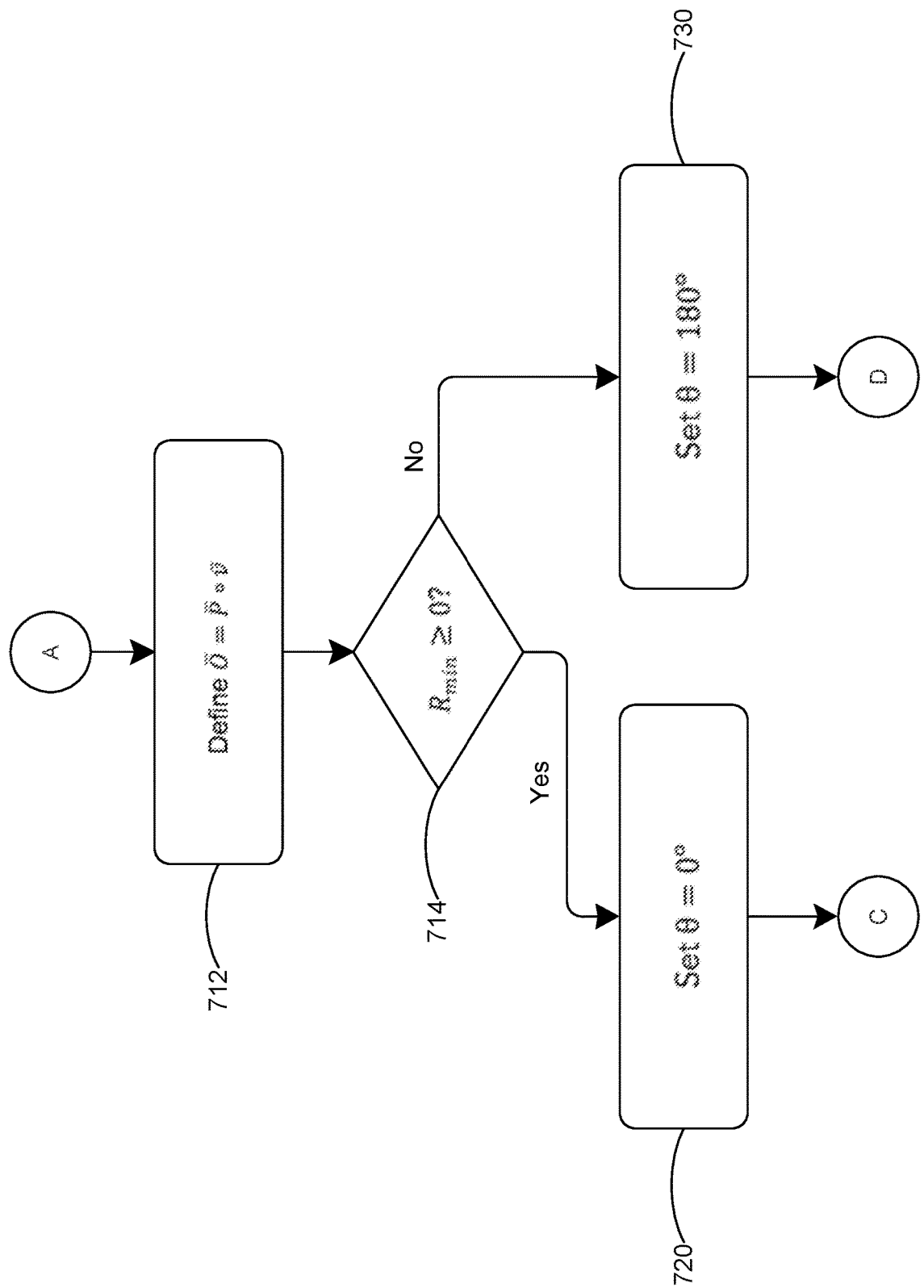

MULTI-CHANNEL REAL-TIME PHASE MODULATION FOR EMI REDUCTION IN AN ULTRASOUND DEVICE

TECHNICAL FIELD

The present application generally relates to ultrasound therapy systems, and more particularly to methods for improving the effectiveness of ultrasound therapy by reducing electromagnetic interference (EMI) arising from ultrasound transducers through the use of phase modulation with respect to the electrical signals sent to such transducers.

BACKGROUND

Ultrasonic transducers have been employed in ultrasound therapy systems to achieve therapeutic heating of diseased and other tissues. Arrays of ultrasound transducers operating to form a beam of ultrasonic energy cause a conversion of sound to thermal energy in the affected tissue areas or treatment volumes, and a subsequent beneficial rise in the temperature in the treatment volumes.

In image-guided ultrasound therapy systems, a patient and the ultrasound therapy apparatus are generally disposed in an imaging volume such as a magnetic resonance imaging (MRI) apparatus, which allows guidance of the applicator placement, and in addition allows monitoring of the treatment effect on the tissue by providing real-time data from which temperature maps can be calculated. A clinical operator can then monitor the progress of the therapy within the treatment volume or diseased tissue and manual or automated changes can be made to the ultrasound power signals based on input from the results and progress of the treatment. With proper monitoring of the heating effect, ultrasound therapy systems can be used to treat harmful cells and to controllably destroy tumors while minimizing damage to healthy tissue.

Work has been done to demonstrate the use of MRI guided transurethral ultrasound therapy systems for treatment of disease such as prostate cancer in men. See, e.g., Chopra, et al., "MRI-compatible transurethral ultrasound system for the treatment of localized prostate cancer using rotational control," Med Phys 35(4):1346-1357, 2008. Also see, U.S. Pub. 2007/0239062; U.S. Pat. No. 6,589,174 "Technique and apparatus for ultrasound therapy," 2003; U.S. Pat. No. 7,771,418, "Treatment of diseased tissue using controlled ultrasonic heating," 2010; U.S. Pat. No. 8,998,889, "System and method for control and monitoring of conformal thermal therapy," 2015; U.S. Pat. No. 9,707,413, "Ultrasonic therapy applicator," 2017. Such systems, including cumulative published and patented work by or for the present applicant, all of which are hereby incorporated by reference, teach the use of transurethral ultrasonic energy to the diseased prostate to reach a desired target temperature in the diseased tissue to achieve the clinical result, which is usually the necrosis of the diseased tissue cells in the prostate. MRI guidance and temperature monitoring of the treatment in real time enables control of the power to the ultrasound therapy transducers as well as control of the rotation of an array of such transducers disposed axially along an elongated applicator inserted into the patient's urethra in the vicinity of the diseased prostate.

As known to those skilled in the art, ultrasonic transducers are constructed and operated to take electrical power and produce ultrasound energy waves from a surface of a transducer element in a process generally referred to as transduction. The nature and extent of the transduction depends on the material used to construct the transducers, transducer geometry, and the electrical input to the transducers. A common material used in construction of ultrasound transducers is piezoelectric transducer crystal material (lead zirconate titanate, PZT), which comes in several forms.

In the systems for ultrasound thermal therapy disclosed in the sources cited above, it is typical to generate radio frequency (RF) electrical output in the bands 4-4.5 MHz and 13-14.4 MHz, and to use this output to drive up to 10 piezoelectric elements that convert the electrical energy into acoustic pressure, i.e. ultrasound. The elements may be driven at a relatively high power, approximately 4 W and 2 W at the low and high bands, respectively, and it is known that PZT material can yield a non-linear response. An effect of this is the generation of electromagnetic interference (EMI) in the form of harmonics that can contaminate MRI images and interfere with MRI thermometry when the transducers are used inside an MRI apparatus, which relies for its operation on RF electromagnetic signals. Such EMI arises from electrical fields generated in the transducer elements, as well as magnetic fields generated by electrical currents flowing to and from the transducer elements, since time-varying electric and magnetic fields can generate electromagnetic radiation, as is well-known in the art.

Thus, there is a need to improve the accuracy and effectiveness of ultrasound thermal therapy by reducing EMI. Traditional shielding methods are not always feasible, or are of limited efficacy, when the sources of the EMI are deployed in narrow spaces inside the human body, for example in the male urethra and prostate. Thus other methods of reducing EMI, which do not increase the bulk of the apparatus deployed, and thus do not risk injury to the patient, are needed. The present disclosure is directed to methods for reducing EMI arising from an array of ultrasound transducers, by adjusting the phase angles of the electrical signals sent to the different transducers in the array.

SUMMARY

The disclosure herein is directed to methods for improving the effectiveness of the use of ultrasound in therapeutic and other procedures by reducing electromagnetic interference arising from an array of ultrasound transducers and the electrical lines connected to such transducers, using phase modulation techniques. The present methods determine and implement phase offset angles for the signals sent to the respective transducers, so as to achieve an optimal degree of reduction of EMI through the mutual offsetting of electrical fields and currents generated by the respective transducers in the array.

An embodiment is directed to a method of reducing electromagnetic interference arising from a set of ultrasound transducers that are part of an array of ultrasound transducers in a thermal therapy apparatus, the set comprising N transducers, each transducer in the set corresponding to an active channel and being electrically driven with a driving signal at an amplitude, a frequency and a phase angle, the frequencies of the driving signals being the same for all transducers in the set, the method comprising a determination and setting of the phase angles $\Theta_1, \Theta_2, \Theta_N$ of each driving signal, the determination and setting of such phase angles comprising determining the amplitudes $A_1, A_2, \ldots, A_N$ of the respective driving signals of each transducer, each amplitude being a nonnegative real number; determining whether one of the amplitudes $A_m$ is greater than the sum of all the amplitudes other than $A_m$, $A_1+A_2+ \ldots A_{m-1}+A_{m+1}+ \ldots +A_N$; if $A_m$ is greater than or equal to the sum of such other amplitudes, setting $\Theta_m = 180°$ and setting $\Theta_i = 0°$ for all i not equal to m; if $A_m$ is less than the sum of such other amplitudes determining a vector $\overline{P}$, such vector comprising N elements, each such element being either 1 or −1, such that the scalar product of $\overline{P}$ and the vector $[A_1, A_2, \ldots, A_N]$ comprising all of the amplitudes is nonnegative and is not greater in magnitude than the magnitude of the scalar product of any other possible vector comprising N elements, each such element being either 1 or −1, and the vector $[A_1, A_2, \ldots, A_N]$ comprising all of the amplitudes; defining a vector $\overline{O}$ comprising N elements, such that each element $O_i$ is equal to the product of $P_i$ and $A_i$, for i=1, 2, ..., N; determining a first positive element of $\overline{O}$, $O_a$, that is not less than any other element of $\overline{O}$; determining a second positive element of $\overline{O}$, $O_b$, that is not less than any other element of $\overline{O}$ save $O_a$; defining a quantity $\gamma$ as the absolute value of the sum of all elements of $\overline{O}$ save $O_a$ and $O_b$; setting $\Theta_a$ and $\Theta_b$ as $$\Theta_a = -\cos^{-1} \frac{O_a^2 + \gamma^2 - O_b^2}{2 O_a \gamma}$$

$$\Theta_b = \cos^{-1} \frac{O_b^2 + \gamma^2 - O_a^2}{2 O_b \gamma}$$

and for all $\Theta_i$, other than $\Theta_a$ and $\Theta_b$, setting $\Theta_i = \cos^{-1} O_i$.

Another embodiment is directed to a method for reducing electromagnetic interference when operating an electrically-driven ultrasound thermal therapy apparatus, comprising positioning said apparatus including an ultrasound array of said apparatus with respect to a specified treatment zone; in a computer-based host unit coupled to said therapy apparatus, determining a common driving frequency and determining an amplitude with which to drive each of a plurality of transducer elements of said array; driving each of said plurality of transducer elements with a respective driving signal generated by a respective voltage source, the driving signal for each element comprising said common driving frequency, said amplitude, and a respective phase angle; and modifying the phase angle of at least one driving signal to reduce a net electromagnetic output of said thermal therapy apparatus.

The treatment zone may be an internal cavity, orifice or other natural or artificial volume within a patient's body, including a urethra, rectum or other organ or cavity. The treatment is delivered internally (for example, transurethrally) in such cases. In other cases the treatment is delivered externally to the body and ultrasonic energy is directed into the body, e.g., through the patient's skin and outer organs and tissue layers. The treatment apparatus can therefore include an array that is linear (along a line or axis of a linear device), or can be a geometrically focused array with a curved, contoured or otherwise geometric arrangement.

IN THE DRAWINGS

For a fuller understanding of the nature and advantages of the present invention, reference is made to the following detailed description of preferred embodiments and in connection with the accompanying drawings, in which:

FIGS. 6A, 6B, 6C and 6D are vector diagrams demonstrating geometrically certain aspects of the methods disclosed herein; and FIGS. 7A, 7B, 7C, and 7D illustrate a flowchart showing the operation of the methods disclosed herein, according to an embodiment.

DETAILED DESCRIPTION

The disclosure herein is directed to methods for using phase modulation techniques to reduce EMI arising from a multi-element array of ultrasound transducers in an apparatus for ultrasound thermal therapy.

Figure 1:
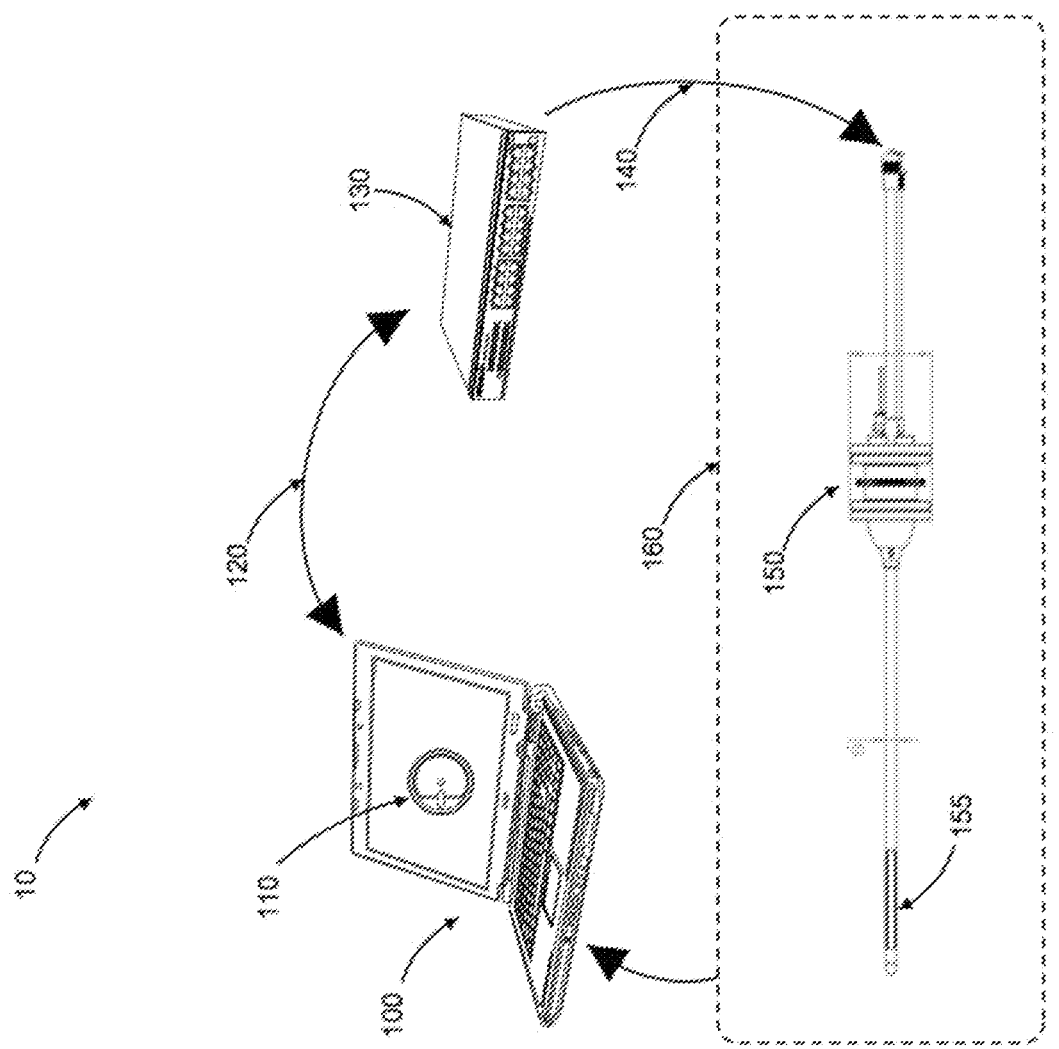
FIG. 1 illustrates an exemplary system for providing image-guided ultrasound therapy to a patient.

FIG. 1 illustrates an exemplary system 10 for providing image-guided ultrasound therapy to a patient. The simplified illustration shows a master computer 100, such as a portable PC, workstation, or other processing device having a processor, memory, and coupled to some input/output apparatus. Master computer 100 may include a display and may support a user interface 110 to facilitate control of and observation of the thermal therapy treatment process.

Master computer 100 is adapted for coupling to other systems and components through a computer interface connector 120. Connection 120 carries data and information to and from master computer 100 and may comprise standard or special-purpose electrical wiring connection cables, such as serial connection cables or the like. Also, connection 120 may be achieved wirelessly as known to those skilled in the art of wireless communication, and may further be achieved by way of multiple connections, over a network, or by another suitable method.

In some embodiments, master computer 100 is coupled through connection 120 to a power control unit 130. Power control unit 130 may be implemented as a stand-alone hardware apparatus but may be implemented as a part of master computer 100, e.g., by being built onto a special card in a computer or server system that accommodates such hardware components.

Power control unit 130 may specifically include at least a processor adapted for processing machine or program instructions, which may be provided to the processor from another component of system 10 and may be stored on a memory device in power control unit 130. Circuitry including analog and/or digital circuitry may be operated within power control unit 130 so as to determine an output power to one or more ultrasound therapy transducer elements in an ultrasound therapy apparatus 150.

In some embodiments, power control unit 130 may deliver controlled electrical driving signals to a plurality of ultrasound transducer elements (e.g., PZT array elements) in ultrasound therapy apparatus 150. The driving signals may be controlled to deliver a programmed amount of power to each element or to groups of elements of therapy apparatus 150. The driving signals may also be controlled so as to provide a determined driving voltage, current, amplitude, waveform, or frequency to said ultrasonic transducers of therapy apparatus 150. The relative phase of the driving signals can also be controlled, for example to reduce EMI, as discussed herein. Such electrical driving signals are carried from power control unit 130 to the ultrasound therapy apparatus 150 over suitable wires, cables, or buses 140. Appropriate plug interfaces or connectors may be included so as to mate the various ends of the connectors or buses to and from their associated components.

In operation, ultrasound therapy apparatus 150 includes a portion 155 that is inserted into a portion of a patient's body to deliver a suitable dose of ultrasound energy to tissue in a diseased region of the patient's body.

The patient and the ultrasound therapy apparatus 150 are generally disposed in an imaging volume 160 such as a magnetic resonance imaging (MRI) apparatus, which can provide real-time images of the relevant parts of the patient, e.g., the treatment volume to master computer 100 or display and user interface 110. In some embodiments, real-time monitoring of the thermal therapy is performed so that a clinical operator can monitor the progress of the therapy within the treatment volume or diseased tissue. Manual or automated changes can be made to the power signals from power control unit 130 based on input from the results and progress of the treatment.

The feedback and coupling of the treatment system components to the control components in system 10 can be used to ensure that an optimum radio frequency (RF) power signal is provided to each element of an ultrasound array 155 used in treatment of diseased tissues. Some examples include treatment of prostate cancer tumors in male patients using MRI guided ultrasound therapy applications.

RF power control unit 130 may include separate circuit cards having individual processors, amplifiers, filters and other components to achieve the desired driving power output to the elements of ultrasound array 155 of ultrasound treatment apparatus 150. Alternatively, a single processor may be employed to control the behavior of the various power channels to each array element.

Figure 2:
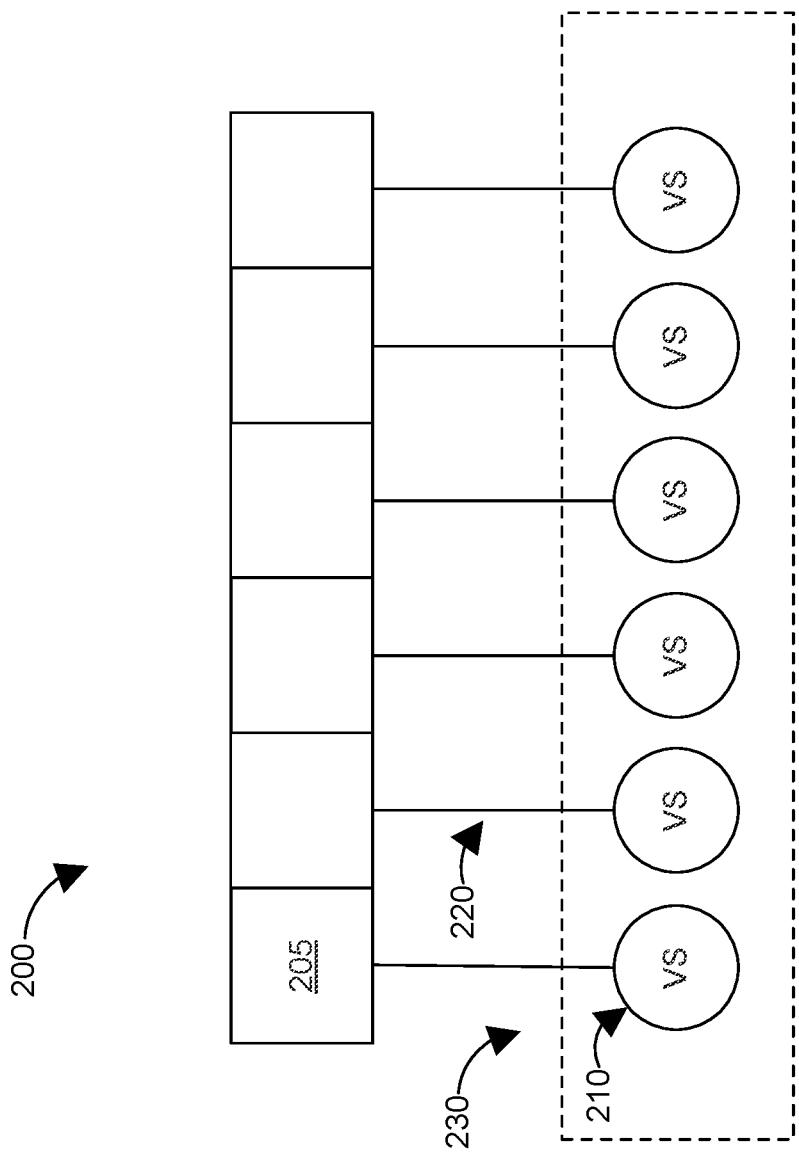
FIG. 2 illustrates an exemplary ultrasound array.

FIG. 2 illustrates an ultrasound array 200, which can be the same as ultrasound array 155. Each ultrasound transducer 205 in ultrasound array 200 is driven by a separate voltage source 210 via at least one electrical line 220. Thus, the voltage and relative phase of each driving signal for each transducer 205 can be controlled. The voltage source 210 are included in RF power control unit 230, which can be the same as RF power control unit 130. It is noted that RF power control unit 230 can include additional components, such as the circuitry, processors, amplifiers, filters, and other components as discussed above with respect to RF power control unit 130.

Each transducer 205 has 2 electrical terminals, the first of which is electrically connected to one terminal of its respective voltage source 210 via an electrical line called a drive line, and the second of which is electrically connected, in common with all the other such second transducer terminals, to the other terminals of the voltage sources 210, via an electrical line called a return line or ground line. The drive lines, one for each ultrasound transducer in the array 200, and the common return line are connected to the proximal end of the applicator and extend to the voltage sources 210. When the apparatus is used for thermal therapy, in a typical arrangement, the applicator will be inserted inside a patient's body to be near a portion of the body receiving the therapy, e.g. inserted transurethrally to be near a diseased male prostate, with the patient inside an MRI machine. The drive lines and return line, typically bound together inside a single sheath, extend from the applicator to outside the MRI machine, where the voltage sources are located, along with the various means for controlling the apparatus, such as RF power control unit 230.

The use of a linear array of transducers, each driven by a separate voltage source, allows more precise control of the application of ultrasound energy to the tissue being treated, thus increasing the effectiveness of the thermal therapy, than would be the case if the transducers were all driven at the same voltage. With separate voltage sources for each transducer, each transducer's voltage amplitude can be dynamically adjusted in response to feedback, in accordance with a treatment plan, to maintain an optimal level of ultrasound output for the location and direction of each transducer at any given time. Systems and methods for controlling and monitoring thermal therapy using ultrasound are described in, for example, U.S. Patent Application Publication No. 2011/0270366, titled "RF Power Controller for Ultrasound Therapy System," and U.S. Pat. No. 8,998,889, titled "System and Method for Control and Monitoring of Conformal Thermal Therapy," which are hereby incorporated by reference.

Each voltage source sends an alternating current (AC) signal, typically a sinusoidal signal, at a given frequency, called the driving frequency, to one of the transducers, at a given voltage amplitude, which amplitude at any given time is determined by the treatment plan and control algorithms and mechanisms of the system. The AC voltage signal causes an oscillating electric field within the transducer, which in turn causes mechanical oscillations in the transducer by means of piezoelectric induction; it is these mechanical oscillations that transmit ultrasound acoustic energy into the tissue being treated, where such energy is ultimately converted into thermal energy to achieve the intended therapeutic effect.

As noted above, EMI inside the MRI apparatus can arise from magnetic fields generated by electrical currents flowing though the driving and return lines, as well as electrical fields generated in the transducers. When multiple transducers are driven at a common driving frequency by separate voltage sources, the EMI from these sources can be reduced by causing voltage signals to be out of phase with each other. In this way, through the principle of superposition, electrical field components that are in opposite directions from each other will superpose and offset each other, as will electrical currents that are in opposite directions from each other. When a plurality of ultrasound transducers are deployed in proximity to one another on a linear array, the electric fields generated by the transducers will partially overlap in space. Similarly, magnetic fields generated by wires that are in close proximity, such as the drive lines, will also overlap in space. Thus in both cases, fields that are in opposite directions will offset, reducing EMI. And the current in the return line is a superposition of the currents from all the transducers, so such currents will directly offset to the extent that they are in opposite directions, thus reducing any resulting magnetic field arising from such currents.

Figure 3:
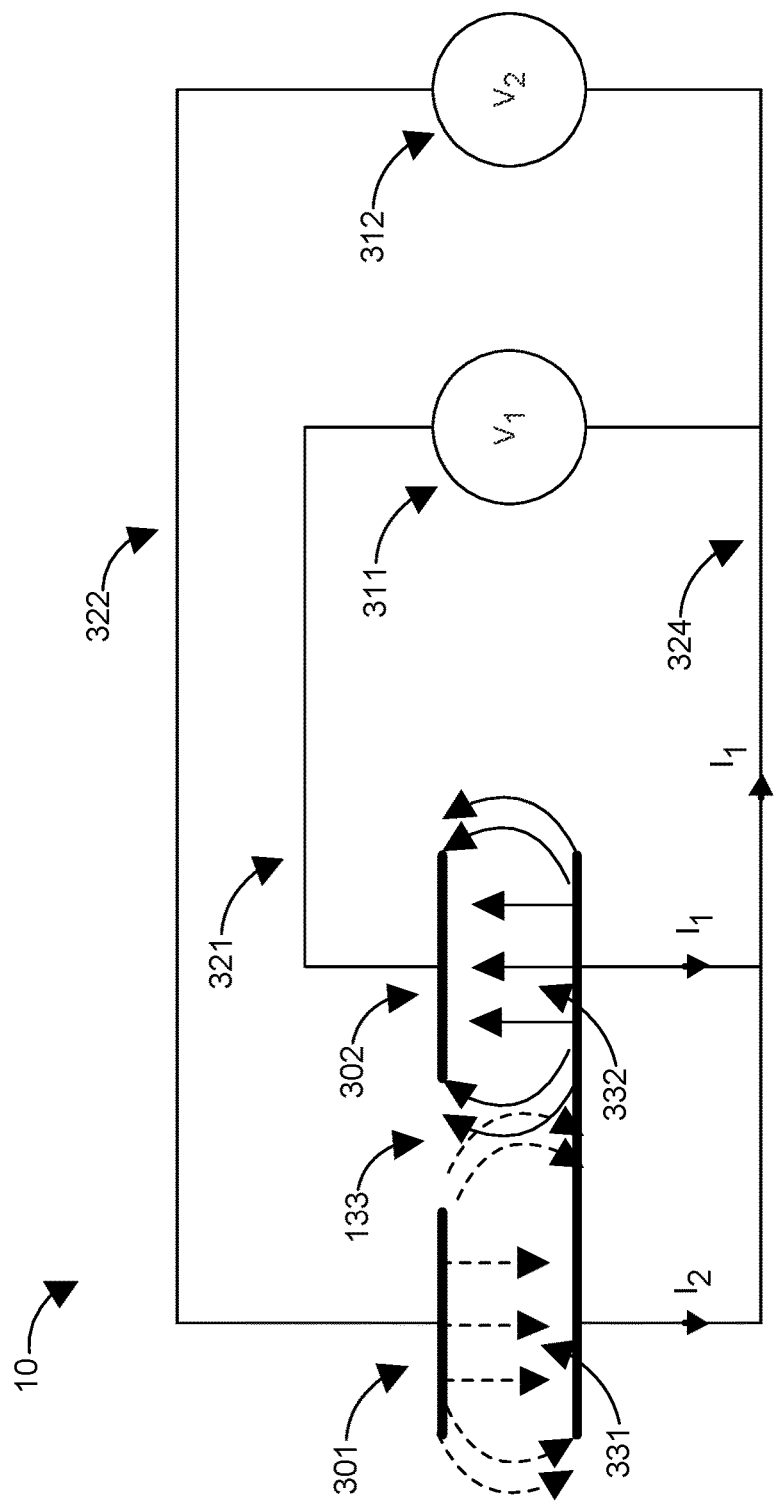
FIG. 3 is a schematic circuit diagram illustrating a simplified model of a two-transducer array, by which certain of the principles underlying the methods disclosed herein are demonstrated.

The principle behind the phase modulation method disclosed herein can be demonstrated by considering a simple case of an array comprising 2 ultrasound transducers driven at a common frequency. FIG. 3 is a simplified schematic diagram showing 2 transducers 301 and 302, each represented as a capacitor, each connected to and powered by one of sinusoidal voltage sources 311 and 312, connected by drive lines 321 and 322 and by shared return line 324. Electric fields within and around the transducers 301 and 302 are shown by field lines 331 and 332, respectively.

The sinusoidal voltage signals emanating from sources 311 and 312 can be described as a function of time as follows:

$$V_1(t) = A \cos(\omega_0 t + \phi_1)$$

$$V_2(t) = B \cos(\omega_0 t + \phi_2)$$

Here, A and B are the voltage amplitudes of the respective signals, $\omega_0$ is the common driving frequency, measured in radians per second, or alternatively in degrees per second, based on a full cycle of $2\pi$ radians or 360 degrees, and $\phi_1$ and $\phi_2$ are the phase angles, or phase offsets, of each signal, measured in radians or alternatively in degrees.

Note that a sinusoidal signal at a given frequency ω can be thought of as a phase vector, or phasor, rotating counterclockwise in the complex plane at a rate of ω radians (or degrees) per second, or one full cycle every $2\pi$ radians (or 360 degrees); the length or magnitude of the vector is the amplitude of the signal, and the signal at any given time is equal to the projection of the phasor onto the horizontal (real) axis, i.e. the real part of the phasor. The phase offset or phase angle of a signal is the angular position of the phasor with respect to the positive real axis, measured counterclockwise from the axis to the phasor, at time t=0, an arbitrary time designated as the start of the cycle, which time is the same for all phasors being considered. When a plurality of AC signals at a common frequency are expressed as phasors, vector arithmetic can be used to compute the combined effect of such signals. The methods disclosed herein make use of such computational techniques.

Turning back to FIG. 3, the currents through the transducers 301 and 302 are designated as $I_1$ and $I_2$, respectively, with the current in the return line 324 designated as $I_T$, with $I_T = I_1 + I_2$. If the phase angles $\phi_1$ and $\phi_2$ are set such that $V_1$ and $V_2$ are in opposite phase, such as by setting $\phi_1 = 0°$ and $\phi_2 = 180°$, and A=B, i.e. the signals are of equal magnitude, then $V_1 = -V_2$ and $I_1 = -I_2$, and the sum $I_T = I_1 + I_2$ will add to zero, i.e. there will be zero net current through the transducers, and zero current in the return line.

This situation is depicted in FIG. 3, where the electric field lines 331 and 332 are shown pointing in opposite directions; the direction of the electric field in the transducer will depend on the sense of the applied voltage. It is assumed that the transducers 301 and 302 are physically parallel to each other, as they would be on a linear transducer array. It can be seen that the electric fields from the respective transducers 301 and 302 overlap in the space 333 between the transducers. By the principle of superposition, such overlapping fields in the same space will offset each other, to the extent that they are pointed in opposite directions. This field cancellation causes a reduction in RF emissions arising from such fields. Additionally, radiation from the return line is reduced, since the return line carries less current and thus generates a smaller magnetic field. Furthermore, magnetic fields generated by the currents in the drive lines will be in opposite directions to each other, as a result of such currents being in opposite directions, and thus such magnetic fields will also superpose and offset each other, further reducing RF emissions.

Piezoelectric materials used in ultrasound transducers, such as PZT, have been observed to exhibit non-linear behavior in response to applied signals. In the simplified case of two active elements, a two-tone non-linear mixing model can be used to understand the resulting harmonic and intermodulation content:

$$V_0 \sim \Sigma_{q=0}^N C_q (V_1 + V_2)^q = C_0 + C_1(V_1 + V_2) + C_2(V_1 + V_2)^2 \ldots$$

Figure 4:
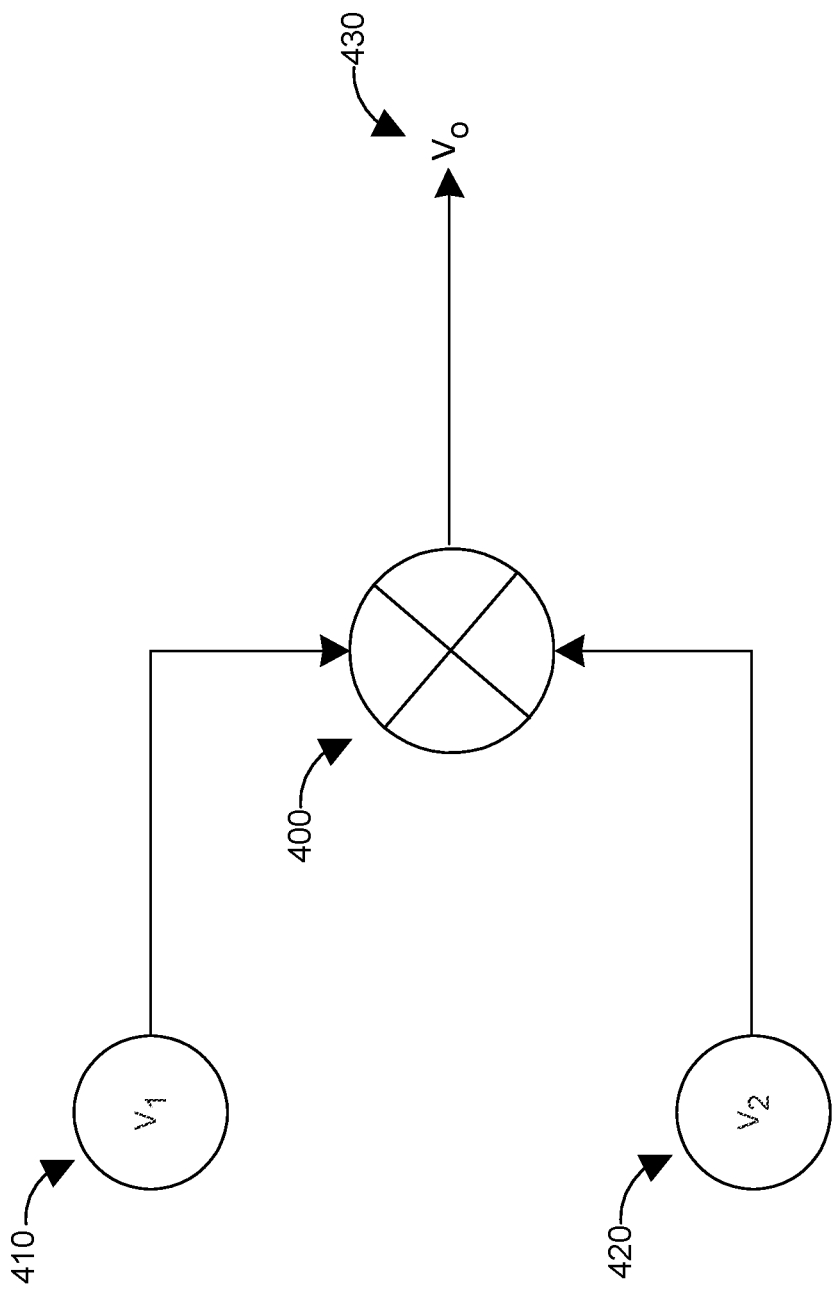
FIG. 4 is a schematic representation of a two-tone mixing model, further demonstrating some of the principles underlying the methods described herein.

In the above equation, $V_1$ and $V_2$ represent the signals applied to the two driven elements, in this case operating at a common frequency of $\omega_0$. The power level is free to vary. $V_0$ is the output of the "mixer" containing the new harmonic and intermodulation content, represented here by a power series approximation of the PZT transfer function. FIG. 4 shows the mixing model in schematic form. Input signals 410 and 420 are fed into mixer 400, which outputs signal 430. For simplicity, model parameters specific to the piezo have been disregarded. In the case where A=B and the signals are in opposing phases, e.g. $\phi_1 = 0°$ and $\phi_2 = 180°$, then $V_1 = V_2$ and the summation terms cancel, eliminating the harmonic content.

Figure 5:
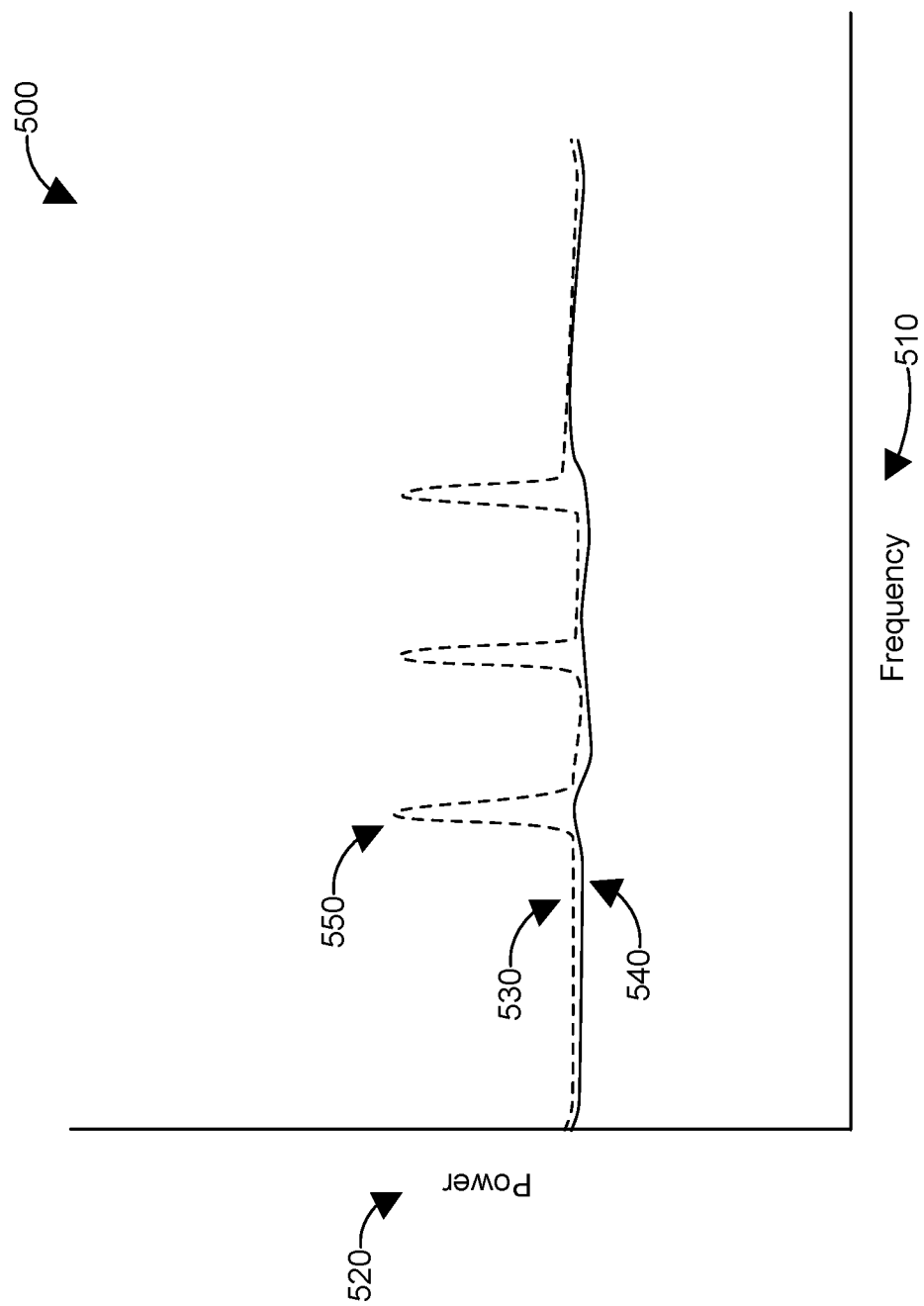
FIG. 5 is an illustrative plot showing the results of two transducers driven both with and without using the methods disclosed herein, demonstrating results obtained from using such methods.

The effect of phase-modulating the signals in the case of two elements can be seen in FIG. 5, which depicts an illustrative plot 500 based on experimental results obtained when driving 2 elements at the same amplitude and frequency, alternatively in-phase and out-of-phase by 180 degrees. The horizontal axis 510 represents frequency, and the vertical axis 520 represents the power of the combined signal. Trace 530 shows the combination of in-phase ($\phi_1 = \phi_2$) driving signals, whereas trace 540 shows the combination of out-of-phase ($\phi_1 + 180° = \phi_2$) driving signals. Peaks 550 represent harmonics, occurring at integral multiples of the driven piezoelectric elements' natural frequency. It can readily be seen that the peaks are substantially lower when the driving signals are out-of-phase, thus demonstrating the substantial reduction of harmonic content resulting from the driving signals being out-of-phase with each other.

The RF voltage signals can be advanced or retarded, that is they can have their phase angle adjusted, without materially affecting the delivery of ultrasound acoustic energy to the target. The ultrasound energy generated by a transducer depends on the amplitude and frequency of the voltage signal driving that transducer, but it does not depend on the phase of that signal; and such energy is transmitted in directions that depend on the location and geometry of the transducer and the surrounding tissue, but that do not depend on the phase of the signal. Thus, the methods disclosed herein, which involve selecting and implementing differing phase angles for the various signals driving an array of ultrasound transducers, are effective to reduce EMI from such signals while maintaining the effectiveness of such signals in driving the transducers to achieve the desired therapeutic ends.

The two-element model discussed above can easily be extended to multiple elements, where one or more subsets of such elements are driven at a common frequency. A simple approach to assigning phase angles would be to set alternating elements at a common frequency to 0/180/0/180 . . . degrees. However, this approach is optimal only when the power output on all elements is identical. In many ultrasound applications, it is desirable to drive different transducer elements on an array at the same frequency but at different power levels, and to dynamically adjust such power levels during a procedure in response to feedback in order to achieve therapeutic or other goals of the procedure. With power levels that vary among transducer elements and over time, a better algorithm is called for.

The method disclosed herein is directed to determining and setting the phase angles of a set of sinusoidal voltage signals driving an array of ultrasound transducers, such that for each subset of signals at a given driving frequency, the vector sum of all signals in such subset is minimized. In computing vector sums, each voltage signal at a given frequency is expressed as a phasor, that is as a vector in the complex plane with a length, or magnitude, equal to the amplitude of the signal, and at an angle, measured counterclockwise from the positive real axis, equal to the phase angle or phase offset of such signal. That is to say, a signal such as $V_1(t)=A_1 \cos(\omega_0 t+\phi_1)$ would be represented in phasor notation as a vector of length $A_1$ pointing at an angle $\phi_1$ counterclockwise from the positive real (i.e. right-pointing) axis. Alternatively, as a vector, the phasor could be represented by its components, i.e. its real and imaginary parts, as $[A_1 \cos \phi_1, A_1 \sin \phi_1]$, or as a single complex number $A_1 \cos \phi_1 + jA_1 \sin \phi_1 = A_1 e^{j\phi_1}$, where $j^2=1$. When expressed in this way, the phasor can be multiplied by $e^{j\omega_0 t}$ to obtain the voltage signal as a function of time: $V_1(t) = \text{Re}\{(A_1 e^{j\phi_1})e^{j\omega_0 t}\} = \text{Re}\{A_1 e^{j(\omega_0 t+\phi_1)}\} = \text{Re}\{A_1 \cos(\omega_0 t+\phi_1) + jA_1 \sin(\omega_0 t+\phi_1)\} = A_1 \cos(\omega_0 t+\phi_1)$. Since all phasors at a given frequency are multiplied by the same factor to obtain the resulting signal, the combined effect of two or more signals at a given frequency can be computed by simply adding the phasors of such signals. Such representation of AC signals is well-known in the electrical arts.

The vector sum of all signals at a given frequency will be a phasor representing the net signal being sent to all transducers in the array that are being driven at that frequency. By minimizing this net signal, net current in the drive and return lines, whose currents are proportional to the voltage signals carried by such lines, will also be minimized. The reduction of net current in the lines will reduce magnetic fields arising from such currents, and thus will reduce RF emissions. Likewise, the reduction of net voltage applied to ultrasound transducer elements that are disposed on a linear array, and thus physically parallel to one another, will result in greater offsetting of electric fields generated by such transducers, and thus reduced RF emissions from such fields.

For a given subset of transducers being driven at a given common frequency, the algorithm disclosed herein can be used to optimize the respective phase angles of the signals to each transducer in the set. Let N be the number of transducers in the subset, and let $A_1$, $A_2$, etc. up to $A_N$ be the respective amplitudes (in voltage, or alternatively power) of the signals to be sent to the transducers in the set; such amplitudes would be determined and selected by whatever means is used for such purpose, in order to achieve the therapeutic and/or other goals of the ultrasound procedure. Note that all $A_i$'s are nonnegative numbers, and will generally be positive for all active channels. (An inactive channel could be represented by a zero amplitude.) The goal is to find a set of phase angles $\theta_1, \theta_2, \ldots, \theta_N$ such that the vector sum of all of the phasors is minimized.

The algorithm proceeds as follows: Define an N-vector (that is, an ordered set of N scalar quantities) $\bar{v}$ consisting of the amplitudes:

$$\bar{v}=[A_1, A_2, \ldots, A_N]$$

As a first pass, or a coarse approximation, we consider only phase angles of 0 and 180 degrees, and what combination of such angles will minimize the overall signal. A phase angle of 180 degrees is equivalent to multiplying the signal by $-1$, simplifying the calculations at this stage. Compute the sum of the amplitudes and determine the maximum amplitude:

$$A_{sum} = \sum_{i=1}^{N} A_i$$

$$A_{max} = \max[A_1, A_2, \ldots, A_N]$$

Determine whether $A_{max} \geq \frac{1}{2} A_{sum}$, i.e. whether the magnitude of the largest element in $\bar{v}$ is greater than or equal to half the sum of all the elements in $\bar{v}$, or in other words the largest amplitude is greater than or equal to the sum of all the other amplitudes. Note that this will always be the case when N=2. The maximum offset of signals that can be achieved by phase modulation is then obtained by setting the phase of the signal with the largest amplitude to 180 degrees, and setting the phase of all other signals to 0 degrees. If $A_{max} = \frac{1}{2} A_{sum}$, then the signals will fully offset, and if $A_{max} > \frac{1}{2} A_{sum}$, then the signals will not fully offset, but will offset to the greatest degree possible for such amplitudes.

It may often be the case, especially when a larger number, e.g. 10, transducers are driven at a given frequency, that the largest amplitude will not be greater than the sum of all the others, i.e. $A_{max} < \frac{1}{2} A_{sum}$. In this case, the next step is to determine the combination of 0 and 180 degree phase angles, or equivalently 1's and $-1$'s, respectively, that will yield the greatest offset of signals. For this purpose, define a "phase offset vector" as a N-vector consisting exclusively of 1's and $-1$'s. (Note that this vector is different from the phase vector or "phasor" discussed above.) There are $2^N$ possible such phase offset vectors, representing all possible permutations of 1's and $-1$'s. For a given phase offset vector $\bar{p}$, the net amplitude, or residual amplitude, resulting from applying the phase angles (0 and 180 degrees) represented by $\bar{p}$, can be computed as the scalar product, also known as the inner product or dot product, of $\bar{v}$ and $\bar{p}$. This product is computed by multiplying the N pairs of corresponding elements in the 2 vectors, and then summing the resulting N products, yielding a scalar result:

$$R=\bar{v}\cdot\bar{p}$$

The next step in the algorithm is to determine a phase offset vector $\bar{p}$ which will yield a residual R with a minimum magnitude, or absolute value:

$$R_{min} = \min_{k=1 \text{ to } 2^N} |\bar{v}\cdot\bar{p}_k|$$

Here, the $p_k$'s are all the possible $2^N$ phase offset vectors. For example, if N=3, $\bar{p}_1$ through $\bar{p}_8$ would be as follows (note that the order here does not matter):

$\bar{p}_1=[-1, -1, -1]$
$\bar{p}_2=[-1, -1, +1]$
$\bar{p}_3=[-1, +1, -1]$
$\bar{p}_4=[-1, +1, +1]$
$\bar{p}_5=[+1, -1, -1]$
$\bar{p}_6=[+1, -1, +1]$
$\bar{p}_7=[+1, +1, -1]$
$\bar{p}_8=[+1, +1, +1]$ $R_{min}$ can be determined by taking the scalar product of $\bar{v}$ with all possible $\bar{p}_k$'s and comparing the results, or by other methods known in the art, such as by using a lookup table, or using an iterative minimization algorithm whose cost function computes the residual under some penalization metric. Note that by symmetry, for each $\bar{p}_k$ there will be another $\bar{p}_k$ with all elements reversed, e.g. in the above list $\bar{p}_2 = -\bar{p}_7$, so the 2 $\bar{p}_k$'s will yield R values of equal magnitude but opposite signs. Thus, since we are interested only in the magnitude of the residual, at most $2^{N-1}$ possibilities need to be checked to determine $R_{min}$.

Let $\bar{P}$=one of the $\bar{p}_k$'s that yields $R_{min}$:

$$\bar{v}\cdot\bar{P}=R_{min}$$

There may be more than one such $\bar{P}$, but any may be selected. By symmetry, for each possible $\bar{P}$ whose inner product with $\bar{v}$ is negative, there will also be another $\bar{P}$ whose inner product with $\bar{v}$ is positive and of the same magnitude, i.e. the first $\bar{P}$ with the signs reversed. Without loss of generality, if $R_{min}>0$, we can arbitrarily choose a $\overline{P}$ that yields a positive inner product with $\overline{v}$. In some embodiments, if there are multiple possible phase offset vectors yielding the same $R_{min}$, then the phase offset vector $\overline{P}$ is selected from these possible candidates based on other criteria, such as seeking to maximize the number of pairs of physically adjacent transducers that are driven in opposite phase to each other.

If $R_{min}=0$, then full offset of the voltage signals may be effected by setting the phase angles of the signals in accordance with $\overline{P}$; that is, if $\overline{P}=[P_1, P_2, \ldots, P_N]$, then each signal from channel i (with amplitude $A_i$) is set to have phase 0 degrees if $P_i=1$, or phase 180 degrees if $P_i=1$.

If $R_{min}>0$, then setting the phase angles in this way, i.e. in accordance with the coarse-approximation step, will not yield full offset of the voltage signals, but will reduce the net signal to one of amplitude $R_{min}$. In this case the algorithm proceeds by taking two of the voltage signals and further adjusting their phase angles so as to achieve full offset from all signals.

We define an N-vector $\overline{O}$ as the element-wise multiplication of $\overline{v}$ with $\overline{P}$, with $\overline{P}$ selected as described above:

$$\overline{O}=\overline{v}\overline{P}=[A_1P_1, A_2P_2, \ldots, A_NP_N]$$

Assuming $\overline{P}$ has been chosen so that $\overline{v}\cdot\overline{P}>0$, as described above, i.e. the sum of the elements of $\overline{O}$ is positive, let $\alpha$ be the largest positive element of $\overline{O}$, with a indexing its position, and let $\beta$ be the next-largest positive element of $\overline{O}$, with b indexing its position:

$$\alpha = O_a = \max_i O_i$$

$$\beta = O_b = \max_{i \neq a} O_i$$

Note that for $R_{min}>0$, there will always be at least 2 positive elements in $\overline{O}$. (If this were not the case, then the one positive element would be larger than the sum of the magnitudes of all the other elements, which is inconsistent with the situation that $A_{max}<\frac{1}{2}A_{sum}$, as discussed above.) Let $\gamma$ be the sum of the remaining elements in $\overline{O}$:

$$\gamma = \sum_{\substack{i=1 \\ i \neq a \\ i \neq b}}^{N} O_i.$$

Note that $R_{min}=\alpha+\beta+\gamma$.

Note that $\gamma$ will be negative. (If $\gamma$ were positive, then $R_{min}$ would not be the smallest possible residual, because it could be made smaller by reversing the signs of both $P_a$ and $P_b$.) Note also that the magnitude of $\gamma$ will be less than the sum of $\alpha$ and $\beta$ (if not, we would have $R_{min}<0$). The magnitude of $\gamma$ will be greater than the difference of $\alpha$ and $\beta$:

$$\gamma<0$$

$$\alpha-\beta<|\gamma|<|\alpha+\beta|$$

The quantity $\gamma$ represents the phasor of the resultant signal of the voltage signal from all the channels except those represented by $\alpha$ and $\beta$. The next step is to set phase angles for those two channels so that they offset that resultant signal. These angles can be found geometrically by forming a triangle with sides of length $\alpha$, $\beta$ and $|\gamma|$. Such a triangle can be formed because the three quantities satisfy the "triangle inequality," above.

The law of cosines states that for any triangle with an angle C opposite a side of length c, with the other sides of length a and b:

$$c^2=a^2+b^2-2ab\cos C$$

With a bit of rearrangement, the law of cosines is used to compute phase angles A and B for the channels represented by $\alpha$ and $\beta$, respectively:

$$A = \cos^{-1}\left(\frac{\beta^2+\gamma^2-\alpha^2}{2|\beta\gamma|}\right)$$

$$B = \cos^{-1}\left(\frac{\alpha^2+\gamma^2-\beta^2}{2|\alpha\gamma|}\right)$$

Channel a is assigned phase angle $-B$, and channel b is assigned phase angle A, with the remaining channels assigned in the coarse-approximation step, i.e. either 0 degrees or 180 degrees depending on whether the corresponding element of $\overline{P}$ is +1 or $-1$, respectively.

The same approach described above can also be used for $R_{min}<0$. In this case, the computations are the same, except that $\alpha$ and $\beta$ are chosen to be the largest (in magnitude) negative elements of $\overline{O}$, and $\gamma$ is positive; and phase angles of channels a and b are assigned to be $180°-B$ and $180°+A$, respectively.

Figure 6C:
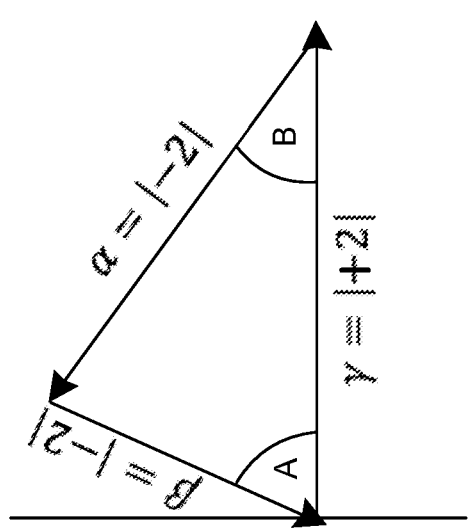

The method of selecting phase angles may be illustrated with a numerical and graphical example. Consider a case where N=4, i.e. 4 active channels, with amplitudes of 1, 1, 3 and 2, respectively, i.e. $\overline{v}=[1, 1, 3, 2]$. It can be determined that the magnitude of the smallest possible residual is 1. $\overline{P}=[-1, -1, +1, 1]$ will generate $R_{min}=1=\overline{v}\cdot\overline{P}$, with $\overline{O}=\overline{v}^o$ $\overline{P}=[-1, -1, +3, -2]$ (Other permutations will also generate $R_{min}=-1$ or $R_{min}=1$, but one is sufficient for the computations.) Thus, the coarse-approximation step yields phase angles of [180°, 180°, 0°, 180°]. This is depicted vectorially in FIG. 6A, with the elements of $\overline{O}$ shown on the top, with the negative elements pointing left and the single positive element pointing right. The residual (R_min) of $-1$ is depicted underneath.

Because the residual is negative, $\alpha$ and $\beta$ are chosen as the two largest vectors in the negative direction, with lengths of $\alpha=2$ and $\beta=-1$, corresponding to channels a=4 and b=1, respectively. FIG. 6B shows the remaining vectors after these 2 vectors are removed, with the new residual $\gamma=+2$ depicted underneath.

The next step is to adjust the phase of the vectors $\alpha$ and $\beta$ to as to offset $\gamma$, i.e. so that the 3 vectors will add vectorially to zero. Applying the law of cosines, $$A = \cos^{-1}\left(\frac{\beta^2+\gamma^2-\alpha^2}{2|\beta\gamma|}\right) = \cos^{-1}\left(\frac{1+1-1}{2(1)(2)}\right) = \cos^{-1}\left(\frac{1}{4}\right) = 75.52°$$

$$B = \cos^{-1}\left(\frac{\alpha^2+\gamma^2-\beta^2}{2|\alpha\gamma|}\right) = \cos^{-1}\left(\frac{4+4-1}{2(2)(2)}\right) = \cos^{-1}\left(\frac{7}{8}\right) = 28.96°$$

Thus we set the phase of channel a as $180°-B=180°-28.96°=151.04°$, and the phase of channel b as $180°+A=180°+75.52°=255.52°$. The vectors $\alpha$ and $\beta$ are shown placed at these angles, with $\gamma$ placed at 0°, in FIG. 6C. Angles A and B are indicated in the triangle formed by the vectors $\alpha$, $\beta$ and $\gamma$. It can be seen that $\alpha$ is at 180° B from the right-pointing (zero phase) position, and that $\beta$ is at $180°+A$ from such position.

Figure 6D:
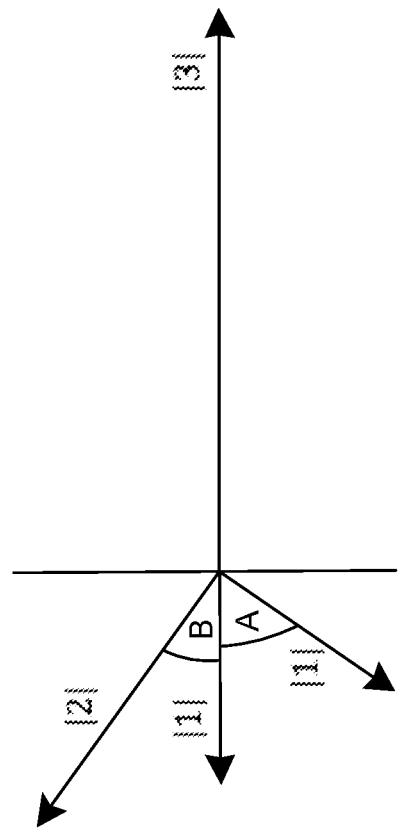

Thus the final phase angles yielded by the method are [255.52°, 180°, 0°, 155.04°]. The phasors represented by the individual channels are shown with these phase angles in FIG. 6D. The vector sum of the 4 phasors is zero, resulting in zero net current in the drive and return lines, and maximum offset of electric fields generated by the transducers.

If the ultrasound transducers on an array are being driven at more than one driving frequency, then the method disclosed herein is performed for each subset of transducers being driven at a given driving frequency. As the amplitudes and driving frequencies are adjusted and recalibrated during the course of the ultrasound procedure, the phase angle computation is repeated each time there is a change in any amplitude and/or frequency for any of the channels. For optimal EMI reduction, each time there is an update in frequencies and/or amplitudes, as determined by the control algorithm and/or treatment plan, the phase angles corresponding to the new set of amplitudes and frequencies are computed as disclosed herein before the change in amplitudes and/or frequencies is implemented in the signals sent to the transducers. Then, when these signals are changed, the new frequencies and amplitudes are implemented concurrently with the new phase angles, determined as disclosed herein.

The method disclosed herein is illustrated in the flowchart 70 depicted in FIGS. 7A-7D. The method begins at step 702, where the N-vector $\bar{v}$ is defined, comprising each of the amplitudes of the N voltage signals at a given driving frequency to be sent to the respective ultrasound transducers in an array. Such amplitudes are determined in accordance with the goals of the ultrasound procedure and in accordance with feedback received and other considerations. These amplitudes are not determined by the method disclosed herein, but are the inputs to such method. The output of the method is a vector $\bar{\theta}=[\theta_1, \theta_2, \ldots, \theta_N]$ comprising phase angles to be used for the voltage signals sent to each transducer.

The method proceeds to step 704, where the dot product (or scalar product) of $\bar{v}$ with each possible $\bar{P}$ vector, that is, each possible N-vector whose elements are either +1 or −1, is computed. Then at step 706 $R_{min}$ is determined from the results of step 704 as the smallest in magnitude dot product computed, and a vector $\bar{P}$, for which $\bar{v} \cdot \bar{P} = R_{min}$, is determined and selected. There may be more than one possible $\bar{P}$ vector that yields $R_{min}$ (or $-R_{min}$), in which case one of such possible $\bar{P}$ vectors is chosen arbitrarily or based on other considerations, such as having adjacent channels with opposite phase offsets for maximal electric field cancellation. Note that for the purpose of this flowchart, $R_{min}$ can be negative or positive. As noted elsewhere herein, in some embodiments $R_{min}$ and $\bar{P}$ may be determined by other methods that do not comprise computing all possible dot products with all possible permutations for $\bar{P}$.

Next is step 708, where it is determined whether the largest amplitude, that is the largest element in $\bar{v}$, is greater than half the sum of all amplitudes. If so, then at step 710 (see FIG. 7D) the phase angles are set in accordance with $\bar{P}$, that is, $\bar{\theta}=\cos^{-1}(\bar{P})$, with the inverse cosine taken element-by-element, so that the phase angle for each channel is either 0° or 180° depending on whether the corresponding element of P is +1 or −1. In some embodiments step 708 takes place before step 704, so that if step 710 is reached, steps 704 and 706 are unnecessary. In such a case, $\bar{\theta}$ would be set such that, if channel m is the channel with the largest amplitude, $\theta_m=180°$ and $\theta_i=0°$ for all i≠m.

If step 708 results in a "no," the flow chart proceeds to placeholder A. FIG. 7B begins with placeholder A, which then proceeds to step 712 $\bar{O}=\bar{P}^o\bar{v}$ is computed, and at step 714 the chart splits into 2 branches depending on whether $R_{min}$ is nonnegative (the "yes" branch)) or negative (the "no" branch). At steps 720 and 730 a scalar quantity Θ, which is used in computing phase angles, is set to be either 0° or 180°. Steps 720 and 730 then proceed to placeholders C and D, respectively.

Figure 7A:
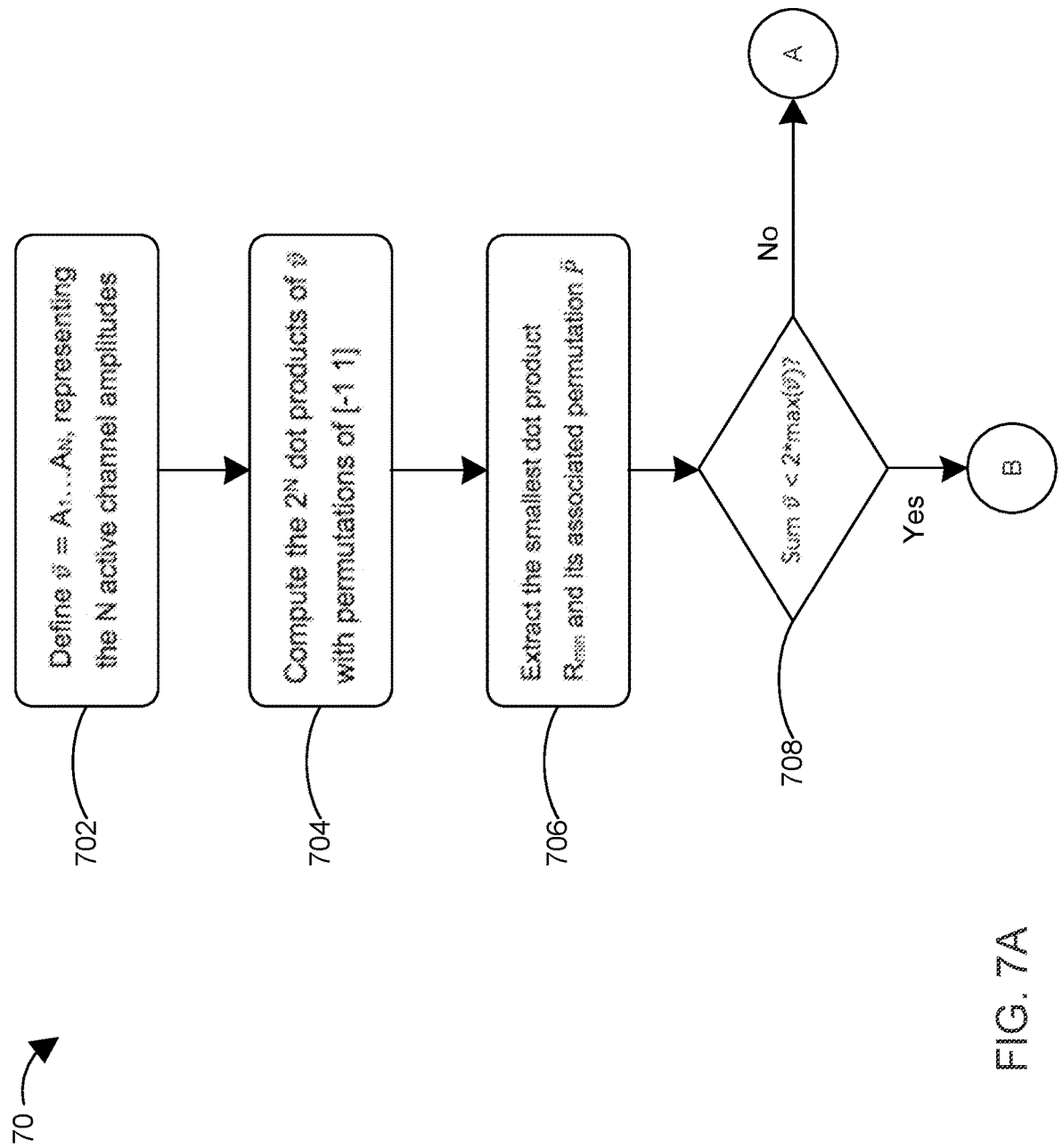
Figure 7C:
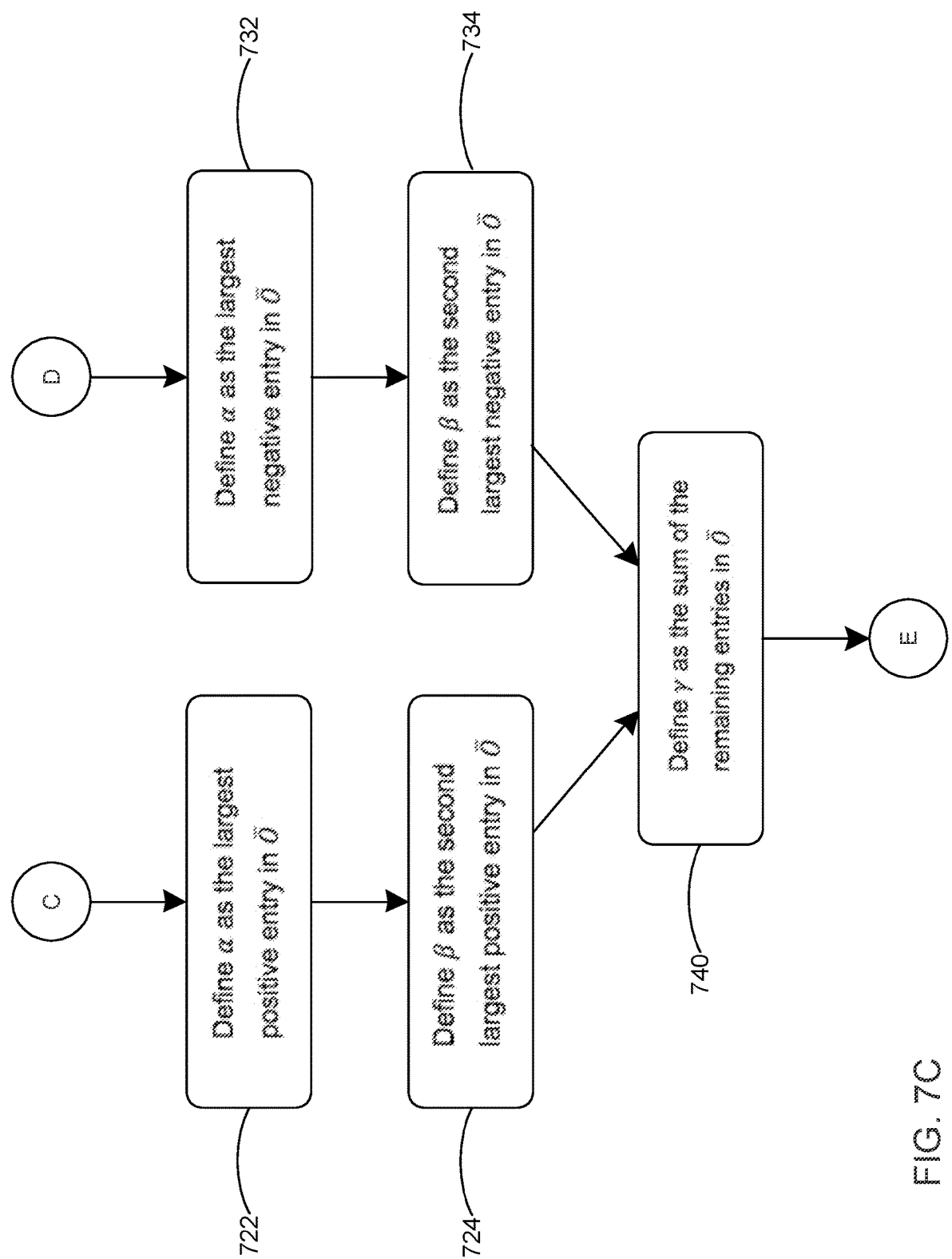
Figure 7D:
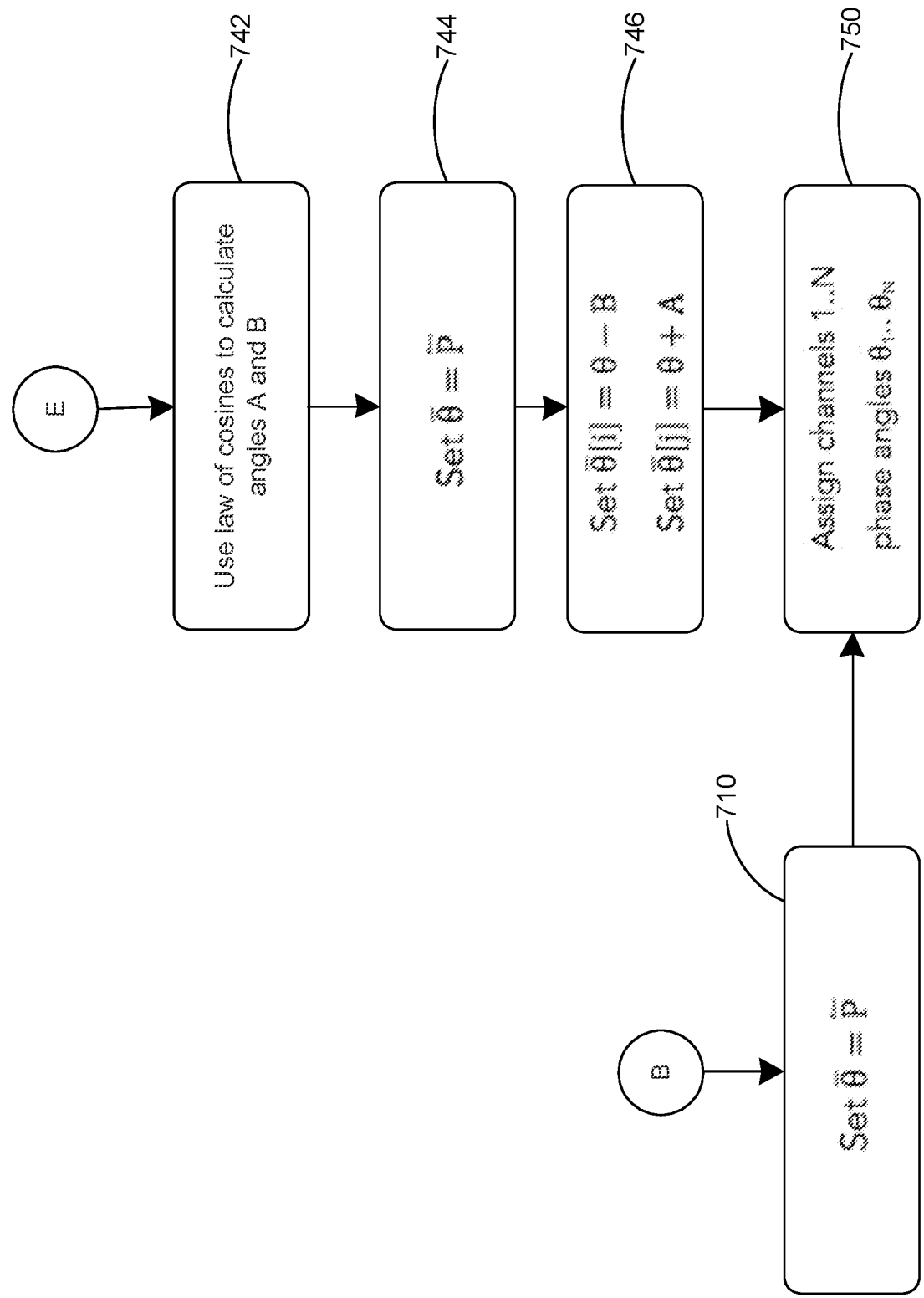

FIG. 7C begins with placeholders C and D. At steps 722 and 732, α is defined as the largest positive (or negative, as the case may be) entry in $\bar{O}$, with its position indexed by i ($\alpha=O_i$). At steps 524 and 534, β is defined as the second largest positive (or negative) entry in $\bar{O}$, with its position indexed by j ($\beta=O_j$).

The branches of the flowchart rejoin at step 540, where the residual γ is defined as the sum of the remaining entries in $\bar{O}$ after removing $O_i$ and $O_j$. Step 540 then proceeds to placeholder E, which is also found in FIG. 7D. Angles A and B and computed from α, β, and γ using the law of cosines at step 542. Specifically, $A=\cos^{-1}([\beta^2+\gamma^2-\alpha^2])/[2\times|\beta|\times|\gamma|])$ and $B=\cos^{-1}([\gamma^2+\alpha^2-\beta^2])/[2\times|\gamma|\times|\alpha|])$.

At step 744 the vector of phase angles $\bar{\theta}$ is temporarily set, in accordance with the coarse-approximation step, as $\cos^{-1}(\bar{P})$. Then at step 746 the phase angles of channels i and j, that is of the vectors $\alpha=O_i$ and $\beta=O_j$, are set in accordance with the angles determined in step 542, so that $\theta_i$ is set to −B if $R_{min}$ is nonnegative, or 180°−B if $R_{min}$ is negative; and $\theta_j$ is set to A if $R_{min}$ is nonnegative, or 180°+A if $R_{min}$ is negative. Note that if $R_{min}=0$, then the computations in step 542 will result in A=B=0, so that the phase angles will all be either 0° or 180°.

From step 746 or step 710, the next step is step 750, wherein the channels 1 through N are assigned phase angles in accordance with the vector $\bar{\theta}$, and such phase angles are implemented in the voltage signals sent to the ultrasound transducers at the amplitudes given by $\bar{v}$. The flow chart 70 can repeat (i.e., return to step 502), at each hardware update interval, i.e. each time there is to be any change in the amplitudes and/or frequencies at which any of the transducers are driven, the method shown in the flowchart is to be followed in order to determine the optimal phase angles to be used with the driving signals, so that such phase angles can be implemented, to the greatest extent feasible, concurrently with the change in amplitudes and/or frequencies.

The present invention should not be considered limited to the particular embodiments described above. Various modifications, equivalent processes, as well as numerous structures to which the present invention may be applicable, will be readily apparent to those skilled in the art to which the present invention is directed upon review of the present disclosure.

What is claimed is:

1. A method for reducing electromagnetic interference when operating an electrically-driven ultrasound thermal therapy apparatus, comprising:
   positioning said apparatus including an ultrasound array of said apparatus with respect to a specified treatment zone;
   in a computer-based host unit coupled to said therapy apparatus, determining a common driving frequency and determining an amplitude with which to drive each of a plurality of transducer elements of said array;
   driving each of said plurality of transducer elements with a respective driving signal generated by a respective voltage source, the driving signal for each element comprising said common driving frequency, said amplitude, and a respective phase angle; and modifying the phase angle of at least one driving signal to reduce a net electromagnetic output of said thermal therapy apparatus, wherein each phase angle is determined based, at least in part, on the amplitude of the corresponding driving signal, wherein before modifying the phase angle of the at least one driving signal, the method further comprises:

(a) multiplying each amplitude and a respective phase offset value of +1 or −1 to determine a respective amplitude-phase product, each phase offset value representing a two-state phase assignment where +1 corresponds to a phase angle of 0 degrees and −1 corresponds to a phase angle of 180 degrees;

(b) summing the respective amplitude-phase products to calculate a residual $R_i$;

(c) repeating steps (a) and (b) for $2^{N-1}$ possible combinations of respective phase offset values to determine a plurality of residuals $R_2N-1$ where N represents a number of the transducer elements in the transducer array; and (d) comparing the residuals $R_2N-1$ to determine a minimum residual $R_{min}$;

wherein modifying the phase angle of the at least one driving signal comprises:

when the minimum residual $R_{min}$ equals 0, setting the respective phase angles according to the two-state phase assignment that corresponds to the minimum residual $R_{min}$.

2. The method of claim 1, further comprising:

before modifying the phase angle of the at least one driving signal and when the minimum residual $R_{min}$ is greater than 0:

comparing the respective amplitude-phase products that correspond to the minimum residual $R_{min}$ to determine a largest amplitude-phase product and a next-largest amplitude-phase product of the respective amplitude-phase products;

calculating a sum of all amplitude-phase products other than the largest and next-largest maximum amplitude-phase products;

wherein modifying the phase angle of at least one driving signal comprises:

setting a phase angle A for the driving signal corresponding to the largest amplitude-phase product as $$A = \cos^{-1}\left(\frac{\beta^2 + \gamma^2 - \alpha^2}{2|\beta\gamma|}\right);$$

setting a phase angle B for the driving signal corresponding to the next-largest amplitude-phase product as $$B = \cos^{-1}\left(\frac{\alpha^2 + \gamma^2 - \beta^2}{2|\alpha\gamma|}\right);$$

and setting the remaining respective phase angles for the respective phase angles other than the phase angles A and B according to the two-state phase assignment that corresponds to the minimum residual $R_{min}$, wherein:

α is the largest amplitude-phase product,

β is the next-largest amplitude-phase product, and

γ is the sum of all amplitude-phase products other than the largest and next-largest maximum amplitude-phase products.

3. The method of claim 2, wherein:

α is $\alpha_p$,

β is $\beta_p$,

γ is $\gamma_p$, and the method further comprises:

before modifying the phase angle of the at least one driving signal and when the minimum residual $R_{min}$ is less than 0:

comparing the respective amplitude-phase products that correspond to the minimum residual $R_{min}$, to determine a first negative amplitude-phase product having a largest magnitude of the respective amplitude-phase products, and a second negative amplitude-phase product having a next-largest magnitude of the respective amplitude-phase products;

calculating a sum of all amplitude-phase products other than the first and second negative amplitude-phase products;

wherein modifying the phase angle of the at least one driving signal comprises:

setting a phase angle C for the driving signal corresponding to the first negative amplitude-phase product as $$C = 180° - \cos^{-1}\left(\frac{\alpha_n^2 + \gamma_n^2 - \beta_n^2}{2|\alpha_n\gamma_n|}\right);$$

setting a phase angle D for the driving signal corresponding to the second negative amplitude-phase product as $$D = 180° + \cos^{-1}\left(\frac{\beta_n^2 + \gamma_n^2 - \alpha_n^2}{2|\beta_n\gamma_n|}\right);$$

and setting the remaining respective phase angles for the respective phase angles other than phase angles C and D according to the two-state phase assignment that corresponds to the minimum residual $R_{min}$, wherein:

$\alpha_n$ is the first negative amplitude-phase product, $\beta_n$ is the second negative amplitude-phase product, and $\gamma_n$ is the sum of all amplitude-phase products other than the first and second negative amplitude-phase products.

* * * * *